United States Patent [19]

Stuchl

[11] Patent Number: 4,754,762
[45] Date of Patent: Jul. 5, 1988

[54] EKG MONITORING SYSTEM

[76] Inventor: Ronald J. Stuchl, 7 N. 421 Garden Ave., Roselle, Ill. 60172

[21] Appl. No.: 765,202

[22] Filed: Aug. 13, 1985

[51] Int. Cl.[4] .............................................. A61B 5/04
[52] U.S. Cl. .................................. 128/696; 128/701; 128/704; 128/712
[58] Field of Search ............... 128/711, 712, 1 D, 670, 128/701, 704, 703, 709, 710, 696

[56] References Cited

U.S. PATENT DOCUMENTS

| | | | |
|---|---|---|---|
| 3,732,868 | 5/1973 | Willems et al. | 128/701 |
| 3,760,100 | 9/1973 | Ragsdale et al. | 128/701 |
| 4,305,400 | 12/1981 | Logan | 128/670 |
| 4,318,412 | 3/1982 | Stanly et al. | 128/696 |
| 4,404,974 | 9/1983 | Titus | 128/670 |
| 4,450,527 | 5/1984 | Sramek | 128/670 |
| 4,509,530 | 4/1985 | Curtis et al. | 128/710 |
| 4,576,178 | 3/1986 | Johnson | 128/670 |
| 4,608,994 | 9/1986 | Ozawa et al. | 128/670 |

FOREIGN PATENT DOCUMENTS

| | | | |
|---|---|---|---|
| 2911035 | 9/1980 | Fed. Rep. of Germany | 128/701 |
| 2054152 | 2/1981 | United Kingdom | 128/701 |
| 1597355 | 9/1981 | United Kingdom | 128/710 |

*Primary Examiner*—William E. Kamm
*Assistant Examiner*—Timothy Keegan

[57] ABSTRACT

An audio-visual EKG monitoring system that segments components of the patient's EKG waveform and synthesizes a plurality of audio driving signals, each representing peak values of the segmented components, and also derives similar peak value signals for driving a CRT bar graph microprocessor.

14 Claims, 2 Drawing Sheets

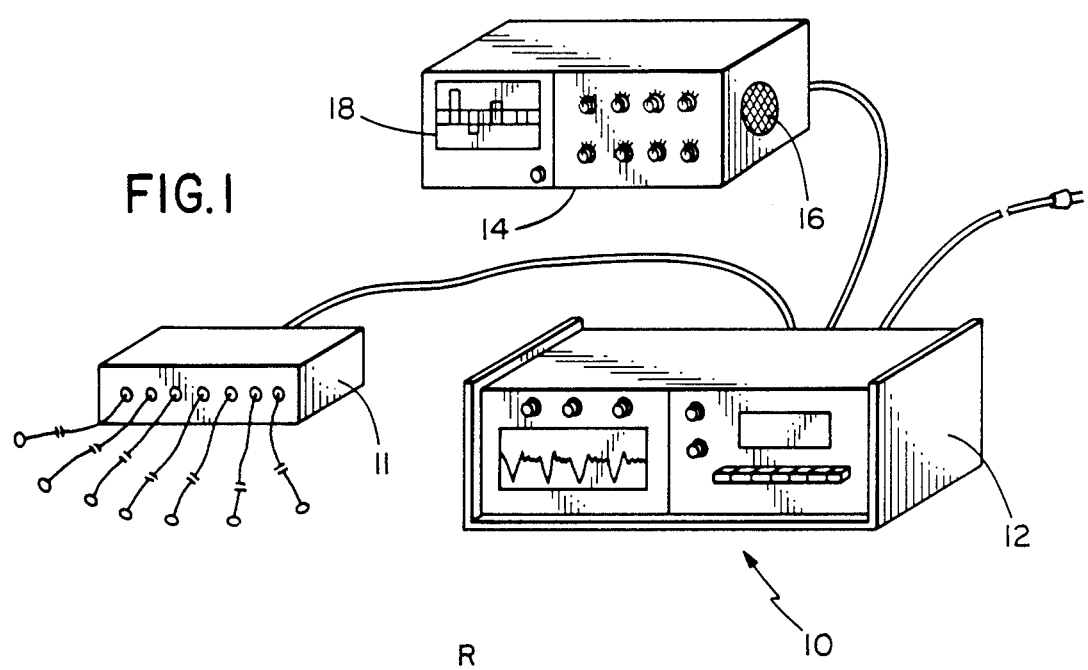
FIG.1
FIG.3
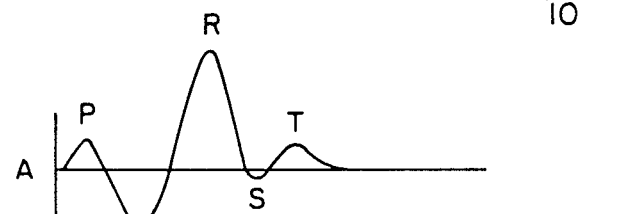
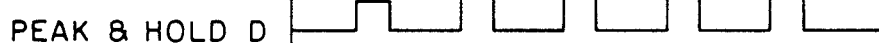
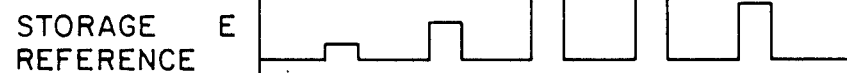
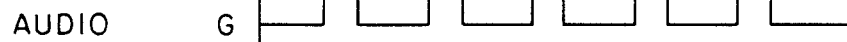

EKG MONITORING SYSTEM

BACKGROUND OF THE INVENTION

Electrocardiography has achieved a significant degree of medical success in the recording and analyzing of the electrical currents produced by the animal and human heart muscle when it contracts and instruments commonly called electrocardiographs have been devised to receive these electrical impulses and record them on an electrocardiogram, usually with a stylus and web-type graph paper, although in recent years cathode ray tubes have been employed to display the electrocardiogram signal. The waveform consists of a complex of waves commonly referred to as the PQRST complex. The initial P-wave represents the beginning of auricular activity and the QRST-waves together represent the onset and procession of ventricular contraction. This information is useful in telling the state of the heart muscle and in diagnosing disturbed heart rhythms. At times it can indicate non-specific heart muscle damage and in other cases it can also diagnose the source of the damage as in coronary thrombosis.

Electrocardiogram instruments insofar as they relate to the signal processing of the electric currents produced by the heart muscle as well as the manner of displaying the signal as processed to the physician have been largely unchanged for the last twenty years, with the exception of the advent of solid-state and IC technology which have simplified and reduced the cost of these instruments but have not significantly modified the signal processing and display functions.

This has been the case in spite of the fact that there has been a profound need to improve the communication link between the EKG monitoring device and the physician. One attempt to improve this communication link has taken the form of a telephone system that enables the EKG waveform to be transmitted over conventional telephone lines into a receiving circuit where the signal is reproduced by a secondary signal demodulating system that usually includes a conventional stylus and web graph paper feeding device for display purposes. Such telephonic monitoring devices are exemplified in the Gombrich et al. U.S. Pat. No. 3,920,005, the Malchman et al. U.S. Pat. No. 3,872,252 and the Pori U.S. Pat. No. 3,886,314. While such telephonic transmission systems have found a reasonable degree of commercial success, all these systems presently known require a receiving demodulating and display device at the telephone receiving location and thus the physician, unless he carries this receiving instrumentation from location to location, is unable to demodulate the EKG signal transmitted with conventional telephone equipment.

There have also been developed in the last decade several fairly sophisticated systems for verifying certain segments of the EKG waveform such as the QRS segment by comparing the segment configuration with stored reference signals, and upon verification storing those so verified and blanking those not verified. Such a system is shown in the Jirak U.S. Pat. No. 4,367,753; however the Jirak system like similar prior EKG monitoring devices uses only conventional display techniques such as an analog chart recorder for displaying the information stored.

Other devices that verify portions of the patient's EKG waveform to compress data or to develop R or S wave peak detection to determine heart rate are found in the Day et al. U.S. Pat. No. 4,109,243 and the Levin U.S. Pat. No. 4,250,889. But again, neither of these proposes any system for altering conventional communication techniques between the EKG signal processing circuitry and the physician.

It is the primary object of the present invention to improve the EKG monitoring and communication systems known in the prior art and discussed generally above.

SUMMARY OF THE PRESENT INVENTION

In accordance with the present invention an improved EKG monitoring system is provided that communicates EKG waveform information to the physician by audio signals played in the same sequence as and representing individual PQRST components. The system also derives a series of visual display signals representing the same PQRST components that drive a bar graph developing microprocessor connected to drive a CRT visual display.

The audio signal synthesizing circuitry separates a conventionally processed EKG analog waveform into equal period PQRST segments, inverts the negative segments or components, and measures the peak value of each component individually. These five peak values are then compared to previously stored values of the patient's PQRST segments and five difference signals are derived therefrom, each proportional to the difference between the stored value and the corresponding just-segmented component. In this way the only information conveyed to the physician is the change in any component and thus he is freed from quantifying information in terms of the patient's history at the time he is given the new information.

These difference signals, five in total, are utilized to derive audio driving signals which are serialized, because of prior buffer storage, in equal period sequence and then utilized to drive audio speakers. What the physician hears then are five repetitive tones, each having a frequency proportional to the difference between the present segmented component and the corresponding stored component.

In the absence of a change or difference signal in any one of the five components, the audio drive circuitry derives five equal tone audio drive signals that are applied serially to the speakers. These reference audio drive signals are phased with the difference audio drive signals. The audio frequency or tone produced by the reference drive signals will be standardized so that it can be recognized throughout the medical field. For example, a 262 Hz. audio signal might be selected and this, of course, corresponds to the middle "C" on the piano. This tone is memorized by physicians through experience so he can easily detect tone changes in the five audio tones, all without requiring any visual attention.

The difference component signals are phased with the reference drive signals and are superimposed on the latter by a summing circuit. The resulting signals are used to drive the speakers so the physician hears the reference tones modified by the difference component signals. For example, if he hears a 162 Hz. audio signal in the "P" position, which is the first tone position of the five tone sequence, he knows the "P" wave has been depressed and with a small amount of experience can quantify or estimate the amount of depression by the tone difference from the reference tone frequency.

As can be appreciated, this audio system enables the physician to direct his visual attention to work other than receiving EKG waveform information. For example, it enables him to engage in uninterrupted surgical activities in the operating room.

Besides that application, the present invention's direct audio performance of EKG waveform change information enables the physician to communicate with the system by conventional remote telephonic equipment without requiring the use of any receiving, decoding, demodulating or display devices.

The present EKG monitoring system also includes circuitry for displaying a five vertical bar graph where each bar represents positive or negative changes in the same individual PQRST components.

BRIEF DESCRIPTION OF THE DRAWINGS

FIG. 1 is a perspective view of the external hardware in the present improved EKG monitoring system;

FIG. 3 is a series of signals found at different locations in the present system.

DETAILED DESCRIPTION OF THE PREFERRED EMBODIMENT

Figure 2:
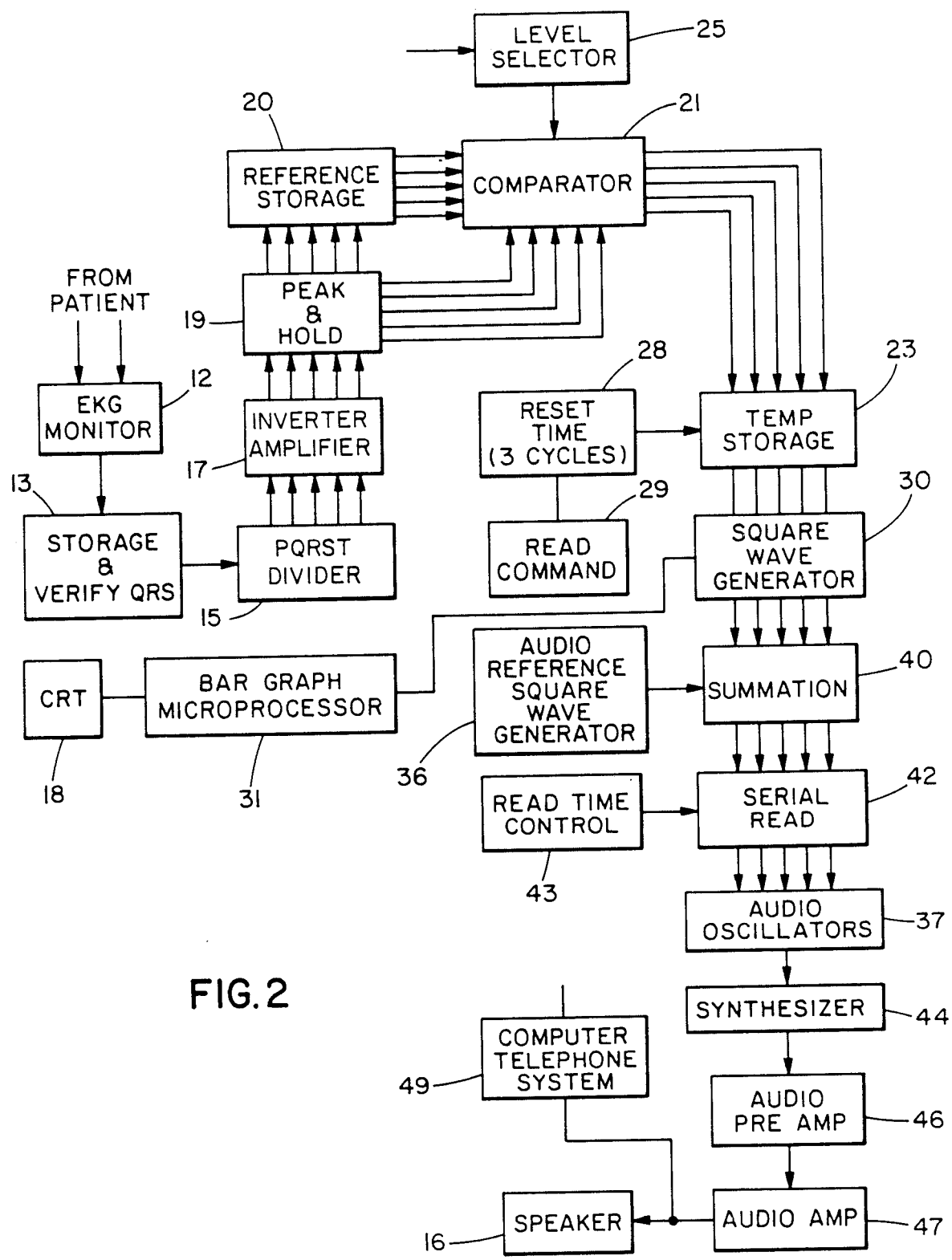
FIG. 2 is a block diagram of the present improved EKG monitoring system including audio and CRT readouts.

Referring to FIG. 1, the present improved EKG monitoring system 10 is seen to generally include a patient connectible electrode housing 12, a conventional EKG signal processor 11 and a visual and audio performance component 14 that includes all of the additional processing circuitry required in the present invention. The component 14 includes a speaker 16 for audibleizing EKG information signals and a CRT 18 for displaying a bar graph, also representing the same EKG information.

Referring to FIG. 2, the EKG monitor 12 receives heart muscle signals from the patient through electrodes and conveys them to a storage and verifying circuit 13 in the component 14 illustrated in FIG. 1. Storage and verifying circuit 13 isolates the QRS component from the remaining portions of the waveform and compares that component to previously stored QRS segments of the same patient to ascertain the validity of the QRS segment. Such systems are by themselves conventional and known in the art.

The partly verified PQRST analog is divided into five equal period components by divider 15. Divider 15 is one of many conventional microprocessor functions. The PQRST complex entering divider 15 is illustrated on line A in FIG. 3 and the partly divided signal is shown in line B with the wave extended so that each component has an equal period. The divider 15 then divides the waveform into five signals and then inverter amplifier 17 inverts the Q and S components which have already been divided and provides the five positive signals indicated on line C in FIG. 3 that are measured in a peak and hold circuit 19 which measures the peak value (illustrated on line D) of each of the five signals and applies them either to a reference storage 20 or a comparator 21.

The reference storage 20 stores the component values that are to be utilized as the standard and may include a floppy disc drive that permits the reference information to be stored for a considerable period of time and then reinserted into the system.

The comparator 21 provides five signals to temporary storage or buffer 23, each proportional to the difference between the individual components in reference storage 20 and the corresponding components in the peak and hold circuit 19.

Level selector 25 permits the operator to select the level at which comparator 21 derives difference signals. The temporary storage 23 eliminates the time base between the five signals and a reset circuitry circuit 28 and a read command 29 permit the remaining portions of the circuit to respond if desired to a divisor of the repeating sequence of five signals. For example, it enables the CRT and the audio circuitry to be driven only by every third sequence of five signals, if desired.

Signals in temporary storage register 23 are each squared by square wave generator 30 and are illustrated in line E of FIG. 3, bearing in mind that each of these signals are simultaneous signals at this point in separate lines. The signals from generator 30 may be either positive or negative depending upon whether there has been an augmentation or diminution in the individual segment component. These signals are utilzied to drive a conventional bar graph microprocessor 31 that displays on CRT 18 a five bar graph that is substantially identical to the waveform illustrated on line E from the square wave generator 30. The physician, for example, viewing the bar graph corresponding to line E in FIG. 3 sees that the P segment has augmented, the Q segment has increased somewhat more, the QRS segment has decreased slightly, the S segment has decreased somewhat more, and the T segment is unchanged. He can consume this information in several seconds without requiring the laborious task of comparing one complex waveform with another.

An audio reference square wave generator 36 provides five reference audio drive signals that are utilized to drive audio oscillators 37 and speaker 16 continuously whether difference signals appear at square wave generator 30 or not. These reference drive signals are illustrated on line G of FIG. 3. The square wave generator 36 provides with the following circuitry five equal, easily recognizable audio tones in repetitive fashion at speaker 16.

Summation circuit 40 algebraically adds the signals from square wave generator 30 to the five equal signals from generator 36 and the resulting five outputs are illustrated on line H of FIG. 3 and these simultaneous signals are sequenced in serial reading device 42 that has a variable period control 43 that controls both the period between the signals and the time of initiation of the signal groups. The five serialized signals are converted to audio driving signals in audio oscillator 37 which in turn may, if desired, be synthesized into more pleasing tones in synthesizer 44, amplified in pre-amps 46 and audio amp 47 and finally utilized to drive speaker 16.

A computer telephone system 49 is provided that enables physicians from remote locations to dial directly into the system and listen to the signals from audio amplifier 47 without the need for any special receiving equipment.

I claim:

1. An EKG monitoring device for developing groups of signals representing the EKG signal complex, comprising: a plurality of patient connectible electrodes for receiving patient derived electrical parameter changes, a signal conditioning and monitoring means for receiving signals from the electrodes and developing a PQRST waveforms complex signal, means for dividing the complex signal into a plurality of segment signals, means for time separating the segment signals into substantially equal periods far greater than the real time periods of the PQRST complex with each segment signal representing one of the PQRST waveforms, means for determining only the maximum amplitude of each segment signal and developing a corresponding number of signals proportional to the amplitudes of the individual segment signals, and means for receiving the amplitude proportional signals serially to produce a human sensory representation of the patient's EKG waveform.

2. An EKG monitoring system as defined in claim 1, including a synthesizer for developing a plurality of sounds from the segment signals, each representing the sound of a different musical instrument.

3. An EKG monitoring system as defined in claim 1, including a telephone system connected to the speaker means whereby the physician can listen to the speaker means from a remote location.

4. An EKG monitoring system as defined in claim 1, including temporary storage means for receiving and storing the segment signals, and means for resetting the storage means after a predetermined period longer than the period between EKG signals whereby only periodic sets of segment signals are utilized to derive audio drive signals.

5. An EKG monitoring device for developing groups of signals representing the EKG signal complex, as defined in claim 1, wherein the means for separating the segment signals includes means for storing the segment signals, and means for serially reading from the storing means.

6. An EKG monitoring device for developing groups of audio signals representing the EKG signal complex, comprising: a plurality of patient connectible electrodes for receiving patient derived electrical parameter changes, a signal conditioning and monitoring means for receiving signals from the electrodes and developing a PQRST complex signal, means for dividing the complex signal into a plurality of segment signals, means for determining the amplitude of each segment signal and developing a corresponding number of audio signals proportional to the amplitudes of the individual segment signals and speaker means for receiving the audio signals serially to produce an audio representation of the patient's EKG waveform and the means for determining the amplitudes of the segment signals including a plurality of peak and hold circuits.

7. An EKG monitoring device for developing groups of audio signals representing the EKG signal complex, comprising: a plurality of patient connectible electrodes for receiving patient derived electrical parameter changes, a signal conditioning and monitoring means for receiving signals from the electrodes and developing a PQRST complex signal, means for dividing the complex signal into a plurality of segment signals, means for determining the amplitude of each segment signal and developing a corresponding number of audio signals proportional to the amplitudes of the individual segment signal, speaker means for receiving the audio signals serially to produce an audio representation of the patient's EKG waveform, the divider circuit dividing the PQRST signal complex into five segment signals, and an inverter for the negative segment signals so that all segment signals are of the same polarity.

8. An EKG monitoring device that provides an audio representation of changes in a patient's cardiac electrical activity, comprising: a plurality of patient connectible electrodes for receiving electrical patient developed signals, an EKG signal conditioning and monitoring means for receiving signals from the electrodes and developing a PQRST complex signal, divider circuit means for receiving the PQRST signal complex and deriving a plurality of segment signals corresponding to portions of the PQRST signal complex, storage means for storing a first set of segment signals as reference signals, comparator means for comparing a second set of segment signals from the divider circuit with corresponding signals in the storage means and deriving therefrom a plurality of difference segment signals, means for deriving a plurality of audio driving signals proportional to the difference segment signals, and speaker means for receiving the audio driving signals.

9. An EKG monitoring device as defined in claim 8, including level selector means for varying the response of the comparator means to the second set of segment signals whereby the threshold values of the difference segment signals can be controlled.

10. An EKG monitoring device as defined in claim 8, including an inverter for receiving the segment signals and achieving unipolarity between the segment signals, means for determining the peak value of the segment signals and deriving peak value segment signals for each of the first and second set of segment signals and applying them to the storage means and comparator means respectively, means for receiving the difference segment signals from the comparator means and deriving a plurality of amplitude varying square wave signals therefrom, means for generating a plurality of reference square wave signals of equal amplitude and applying them to the means for deriving a plurality of audio driving signals so that in the absence of difference segment signals the equal reference square wave signals will be heard from the speakers, and summation circuit means for combining the reference square wave signals and the difference segment square wave signals so that the audio driving signals represent a combination of both.

11. An EKG monitoring system as defined in claim 8 including means for generating a plurality of equal reference audio driving signals and apply them to the speaker means so that in the absence of any difference segment signals the reference audio driving signals will be heard, and summation means for the equal reference audio driving signals and the audio driving signals from the difference segment signals so that in the presence of any difference segment signals the audio from the speaker means is an algebraic combination of the two.

12. An EKG visual monitoring device, comprising: a plurality of patient connectible electrodes for receiving electrical patient derived signals, an EKG signal conditioning and monitoring means for receiving signals from the electrodes to develop a PQRST complex signal, divider circuit means for receiving the PQRST signal complex and deriving a plurality of segment signals corresponding to portions of the PQRST signal complex with each segment signal representing one of the PQRST waveforms, means for only deriving a plurality of amplitude segment signals proportional to the maximum amplitude of the segment signals, means for representing the amplitude segment signals into substantially equal periods far greater than the real time periods of the PQRST complex, means for developing a plurality of CRT driving signals, each proportional to the amplitude of one of the amplitude segment signals, and CRT visual display means for receiving the CRT drive signals and displaying a plurality of vertical bars, each proportional in height to the amplitude of a portion of the PQRST signal complex.

13. An EKG visual monitoring device as defined in claim 12 including means for deriving audio driving signals from the amplitude segment signals, and speaker means for receiving the audio driving signals.

14. An EKG monitoring device that provides a representation of changes in a patient's cardiac electrical activity, comprising: a plurality of patient connectible electrodes for receiving electrical patient developed signals, an EKG signal conditioning and monitoring device for receiving signals from the electrodes and developing a PQRST complex signal, divider circuit means for receiving the PQRST signal complex and deriving a plurality of segment signals corresponding to portions of the PQRST signal complex, storage means for storing a first set of segment signals as reference signals, comparator means for comparing a second set of signals from the divider circuit with corresponding signals in the storage means and deriving therefrom a plurality of difference segment signals, means for deriving a plurality of driving signals proportional to the difference segment signals, and means for receiving the driving signals and providing human sensory performance means therefrom.

* * * * *